US008187611B2

(12) United States Patent
Abboud et al.

(10) Patent No.: US 8,187,611 B2
(45) Date of Patent: May 29, 2012

(54) **ANTI-PEPTIDE ANTIBODIES THAT CROSS REACT WITH PROTECTIVE ANTIGEN OF *BACILLUS ANTHRACIS* AND USES THEREOF**

(75) Inventors: Nareen Abboud, New Rochelle, NY (US); Arturo Casadevall, New Rochelle, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 12/924,813

(22) Filed: Oct. 5, 2010

(65) Prior Publication Data

US 2011/0171223 A1 Jul. 14, 2011

Related U.S. Application Data

(60) Provisional application No. 61/280,012, filed on Oct. 29, 2009.

(51) Int. Cl.
*A61K 39/07* (2006.01)
*A61K 39/02* (2006.01)
*A61K 39/00* (2006.01)
*A61K 38/00* (2006.01)

(52) U.S. Cl. ............... 424/246.1; 424/190.1; 424/234.1; 424/184.1; 424/192.1; 424/236.1; 514/1.1; 530/300; 530/825

(58) Field of Classification Search ................ None
See application file for complete search history.

(56) References Cited

U.S. PATENT DOCUMENTS 7,179,645 B2 * 2/2007 Humphreys et al. ....... 435/320.1
7,794,732 B2 * 9/2010 James et al. ............... 424/246.1
2003/0170263 A1 * 9/2003 Williamson et al. ....... 424/190.1
2004/0009945 A1 * 1/2004 Lee et al. ..................... 514/44
2005/0245454 A1 * 11/2005 Goldstein ..................... 514/14
2009/0104214 A1 * 4/2009 Neri et al. ................... 424/185.1
2011/0256172 A1 * 10/2011 Cease et al. ................. 424/197.11

OTHER PUBLICATIONS

Tam. PNAS 85: 5409-5413, 1988.*
Huang et al. Mol. Immunol. 31: 1191-1199, 1994.*
Abboud N., et al.; Identification of Linear Epitopes in *Bacillus anthracis* Protective Antigen Bound by Neutralizing Antibodies; The Journal of Biological Chemistry, vol. 284, No. 37, pp. 25077-25086, Sep. 11, 2009, electronically published Jul. 18, 2009.*
Rivera J, et al.; A Monoclonal Antibody to *Bacillus anthracis* Protective Antigen Defines a Neutralizing Epitope in Domain 1; Infection and Immunity, vol. 74, No. 7, p. 4149-4156, Jul. 2006.*
Abboud N, et al.; Immunogenicity of *Bacillus anthracis* Protective Antigen Domains and Efficacy of Elicited Antibody Responses Depend on Host Genetic Background; Clinical and Vaccine Immunology, vol. 15, No. 7, p. 1115-1123, Jul. 2008.*

* cited by examiner

*Primary Examiner* — S. Devi
(74) *Attorney, Agent, or Firm* — Amster, Rothstein & Ebenstein LLP

(57) ABSTRACT

The present invention provides a purified peptide comprising at least one of the sequences LKQKSSNSRKKRSTS (SEQ ID NO:1), or VKNKRTFLSPWISNI (SEQ ID NO:2) as well as a vaccine, a method to protect or treat an animal from anthrax toxin, a method of making a vaccine and the use of the peptide. The present invention also provides a monoclonal antibody that specifically binds to a peptide sequence comprising at least one of the following peptide sequences: LKQKSSNSRKKRSTS (SEQ ID NO:1), or VKNKRTFLSPWISNI (SEQ ID NO:2) as well as a method to protect or treat an animal from anthrax toxin, a method of making a vaccine, a pharmaceutical composition, a method of making a pharmaceutical composition, and the use of the monoclonal antibody.

15 Claims, 10 Drawing Sheets

A

US 8,187,611 B2

ANTI-PEPTIDE ANTIBODIES THAT CROSS REACT WITH PROTECTIVE ANTIGEN OF *BACILLUS ANTHRACIS* AND USES THEREOF

CROSS-REFERENCE TO RELATED APPLICATION

This application claims the benefit of U.S. Provisional Application No. 61/280,012, filed Oct. 29, 2009, the contents of which are herein incorporated by reference.

STATEMENT OF GOVERNMENT SUPPORT

This invention was made with government support under grant numbers 2U54AI057158-06 awarded by the National Cancer Institute, National Institutes of Health, U.S. Department of Health and Human Services, and DOD-071640041 awarded by the Department of Defense. The government has certain rights in the invention.

FIELD OF THE INVENTION

The present invention relates generally to peptides that elicit neutralizing antibodies to anthrax toxin and uses thereof.

BACKGROUND OF THE INVENTION

Throughout this application various publications are referred to in brackets. Full citations for these references may be found at the end of the specification. The disclosures of these publications are hereby incorporated by reference in their entirety into the subject application to more fully describe the art to which the subject invention pertains.

*Bacillus anthracis* is a gram-positive, facultatively anaerobic, rod-shaped bacterium that is the causative agent of anthrax. It secretes two toxins which are composed of three proteins: protective antigen (PA), edema factor (EF) and lethal factor (LF). The anthrax toxins, like other binary toxins, have distinct subunits involved in the different steps of the toxin's action. The B subunit (PA) is involved in receptor binding and cellular internalization into the cytoplasm, whereas the A subunit (EF and/or LF) bears the enzymatic activity [1]. Anthrax can occur naturally in animals by spore transmission via ingestion, inhalation, or an open skin wound, but it can also be a result of bioterrorism and biological warfare [2].

PA is the component of the currently licensed anthrax vaccine (AVA) that elicits protective antibodies. Recent studies have demonstrated that a strong humoral response to truncated recombinant PA contributes to a protective immune response to anthrax [3, 4]. Accordingly, there is considerable interest in ascertaining the location and immunogenicity of B-cell epitopes on the PA molecule. The development of numerous monoclonal antibodies (mAb) to different epitopes on the PA molecule that influence PA functions, in conjunction with epitope mapping, have provided an opportunity to study the fine antigenic structure of PA. Most of these epitopes have been defined in mice [5-8], in macaques [9], in rabbits [10], as well as in vaccinated humans [11]. Consequently, the epitopes described thus far are localized to three discrete regions within PA. These regions correspond to the 2β2-2β3 loop of domain 2, the domain 3-domain 4 boundary and the small loop of domain 4. The 2β2-2β3 loop of domain 2 is responsible for mediating membrane insertion and many neutralizing murine mAbs target this region [5, 8]. The boundary between domains 3 and 4, which does not have a known functional activity, has been suggested as a region recognized by polyclonal antibodies from vaccinated humans and rabbits [6, 12]. The cellular receptor binding region is localized to the small loop of domain 4, and this region has been described to be recognized by two neutralizing mAbs [7, 9]. With the exception of a neutralizing mAb that bound to PA20 [13], no B-cell epitopes have been reported in domain 1. Therefore, identification of further dominant antigenic epitopes is pivotal for understanding the minimal immunogenic region of PA that will allow for precise direction of potent immune responses.

There is an urgent need for a more effective prophylactic vaccine against anthrax. The treatment of anthrax remains unsatisfactory because of high morbidity and mortality [2] and there are significant drawbacks to the currently licensed vaccine. Consequently, there is considerable interest in the development of passive immune therapies and more effective vaccines. Additionally, anthrax toxin has the ability to impair innate and adaptive immune responses, entering the cytosol of every cell type and altering their signaling pathways, which in turn inhibits the clearance of the bacterium [23]. The present invention answers this need.

SUMMARY OF THE INVENTION

The present invention provides a purified peptide comprising the sequence LKQKSSNSRKKRSTS (SEQ ID NO:1). The present invention also provides a purified peptide comprising the sequence VKNKRTFLSPWISNI (SEQ ID NO:2).

The present invention further provides a vaccine comprising a multiple antigenic peptide comprising the sequence LKQKSSNSRKKRSTS (SEQ ID NO:1). The present invention additionally provides a vaccine comprising a multiple antigenic peptide comprising the sequence VKNKRTFLSPWISNI (SEQ ID NO:2).

The present invention provides a monoclonal antibody that specifically binds to a peptide sequence comprising at, least one of the following peptide sequences: LKQKSSNSRKKRSTS (SEQ ID NO:1), or VKNKRTFLSPWISNI (SEQ ID NO:2).

The present invention also provides a method to protect or treat an animal from anthrax toxin, the method comprising administering a vaccine comprising at least one of the following multiple antigenic peptides: a multiple antigenic peptide comprising the sequence LKQKSSNSRKKRSTS (SEQ ID NO:1), or a multiple antigenic peptide comprising the sequence VKNKRTFLSPWISNI (SEQ ID NO:2). The present invention further provides a method to protect or treat an animal from anthrax toxin, the method comprising administering a pharmaceutical composition comprising a monoclonal antibody that specifically binds to at least one of the following peptide sequences: LKQKSSNSRKKRSTS (SEQ ID NO:1) or VKNKRTFLSPWISNI (SEQ ID NO:2).

The present invention provides a method of making a vaccine comprising formulating a multiple antigenic peptide comprising at least one of the following sequences: LKQKSSNSRKKRSTS (SEQ ID NO:1) or VKNKRTFLSPWISNI (SEQ ID NO:2) in dosage form for treating or protecting an animal from anthrax toxin. The present invention additionally provides a method of making a pharmaceutical composition comprising formulating a monoclonal antibody that specifically binds to at least one of the following sequences: LKQKSSNSRKKRSTS (SEQ ID NO:1) or VKNKRTFLSPWISNI (SEQ ID NO:2) in dosage form for treating or protecting an animal from anthrax toxin.

The present invention provides for the use of at least one of the following sequences: LKQKSSNSRKKRSTS (SEQ ID NO:1) or VKNKRTFLSPWISNI (SEQ ID NO:2) for preparing a vaccine to treat or protect an animal from anthrax toxin. The present invention also provides for the use of a monoclonal antibody that specifically binds to at least one of the following sequences: LKQKSSNSRKKRSTS (SEQ ID NO:1) or VKNKRTFLSPWISNI (SEQ ID NO:2) for preparing a pharmaceutical composition to treat or protect an animal from anthrax toxin.

The present invention additionally provides for a pharmaceutical composition comprising a monoclonal antibody that specifically binds to at least one of the following sequences: LKQKSSNSRKKRSTS (SEQ ID NO:1) or VKNKRTFLSPWISNI (SEQ ID NO:2) and a pharmaceutically acceptable carrier.

DETAILED DESCRIPTION OF THE INVENTION

Figure 1:
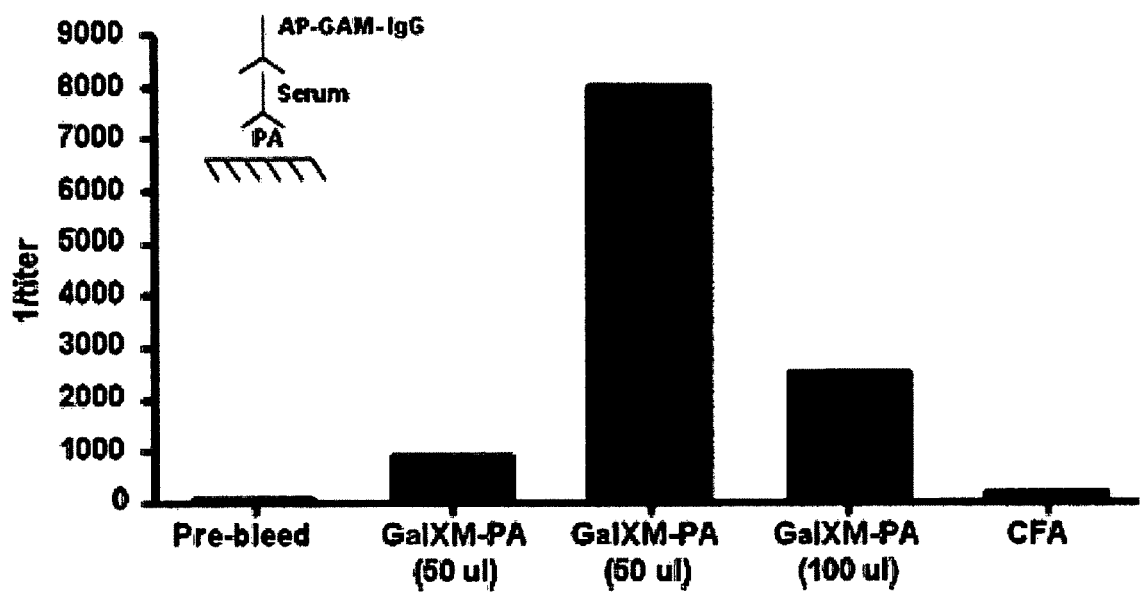
FIG. 1. Inverse antibody titers of BALB/c mice immunized with GalXM-PA conjugate as measured by ELISA. Two of the five female BALB/c mice (each bar represents one mouse) were initially immunized with 50 μl and one mouse was immunized with 100 μl of GalXM-PA conjugate in CFA on day 0. All mice were boosted with 50 μl of the conjugate in IFA at day 14. Sera were assayed for IgG anti-PA antibodies by ELISA. Insert, schematic of ELISA configuration used.

The present invention provides a purified peptide comprising the sequence LKQKSSNSRKKRSTS (SEQ ID NO:1). The present invention also provides a purified peptide comprising the sequence VKNKRTFLSPWISNI (SEQ ID NO:2).

The present invention further provides a vaccine comprising a multiple antigenic peptide comprising the sequence LKQKSSNSRKKRSTS (SEQ ID NO:1). The present invention additionally provides a vaccine comprising a multiple antigenic peptide comprising the sequence VKNKRTFLSPWISNI (SEQ ID NO:2).

The present invention provides a monoclonal antibody that specifically binds to a peptide sequence comprising at least one of the following peptide sequences: LKQKSSNSRKKRSTS (SEQ ID NO:1), or VKNKRTFLSPWISNI (SEQ ID NO:2).

The present invention also provides a method to protect or treat an animal from anthrax toxin, the method comprising administering a vaccine comprising at least one of the following multiple antigenic peptides: a multiple antigenic peptide comprising the sequence LKQKSSNSRKKRSTS (SEQ ID NO:1), or a multiple antigenic peptide comprising the sequence VKNKRTFLSPWISNI (SEQ ID NO:2).

The present invention further provides a method to protect or treat an animal from anthrax toxin, the method comprising administering a pharmaceutical composition comprising a monoclonal antibody that specifically binds to at least one of the following peptide sequences: LKQKSSNSRKKRSTS (SEQ ID NO:1) or VKNKRTFLSPWISNI (SEQ ID NO:2).

The present invention provides a method of making a vaccine comprising formulating a multiple antigenic peptide comprising at least one of the following sequences: LKQKSSNSRKKRSTS (SEQ ID NO:1) or VKNKRTFLSPWISNI (SEQ ID NO:2) in dosage form for treating or protecting an animal from anthrax toxin.

The present invention additionally provides a method of making a pharmaceutical composition comprising formulating a monoclonal antibody that specifically binds to at least one of the following sequences: LKQKSSNSRKKRSTS (SEQ ID NO:1) or VKNKRTFLSPWISNI (SEQ ID NO:2) in dosage form for treating or protecting an animal from anthrax toxin.

The present invention provides for the use of at least one of the following sequences: LKQKSSNSRKKRSTS (SEQ ID NO:1) or VKNKRTFLSPWISNI (SEQ ID NO:2) for preparing a vaccine to treat or protect an animal from anthrax toxin. The present invention also provides for the use of a monoclonal antibody that specifically binds to at least one of the following sequences: LKQKSSNSRKKRSTS (SEQ ID NO:1) or VKNKRTFLSPWISNI (SEQ ID NO:2) for preparing a pharmaceutical composition to treat or protect an animal from anthrax toxin.

The present invention further provides a pharmaceutical composition comprising a monoclonal antibody that specifically binds to at least one of the following sequences: LKQKSSNSRKKRSTS (SEQ ID NO:1) or VKNKRTFLSPWISNI (SEQ ID NO:2) and a pharmaceutically acceptable carrier.

In any embodiment of the present invention, the peptide sequence can consist essentially of LKQKSSNSRKKRSTS (SEQ ID NO:1) or VKNKRTFLSPWISNI (SEQ ID NO:2). Additionally, in any embodiment, the peptide sequence can consist of LKQKSSNSRKKRSTS (SEQ ID NO:1) or VKNKRTFLSPWISNI (SEQ ID NO:2).

A peptide epitope is the portion of a macromolecule which is recognized by the immune system. LKQKSSNSRKKRSTS (SEQ ID NO:1) and VKNKRTFLSPWISNI (SEQ ID NO:2) are epitopes of protective antigen (PA) protein, one of three proteins in the anthrax toxin. When an animal is exposed to these epitopes, the animal's immune system synthesizes antibodies. Upon exposure to anthrax, the antibodies recognize the peptide epitopes, which are a portion of PA located on the surface of anthrax. This allows the animals to mount an immune response to anthrax. LKQKSSNSRKKRSTS (SEQ ID NO:1) and VKNKRTFLSPWISNI (SEQ ID NO:2) can be used, separately or together, in an epitope-based anthrax vaccine.

The multiple antigenic peptide system (MAP) utilizes a lysine backbone with multiple peptide epitopes attached. Any number of copies of the peptide epitope can be attached to a single back bone. Preferably between two and fourteen copies of the peptide epitope are attached to a single backbone. More preferably, between four and ten copies of the peptide epitope are attached to a single backbone. Most preferably, eight copies of the peptide epitope are attached to a single backbone. MAP produces a strong immune response to the peptide epitope. For an effective vaccine, LKQKSSNSRKKRSTS (MAP-SEQ ID NO:1) or MAP-VKNKRTFLSPWISNI (SEQ ID NO:2) are used instead of the singular peptide epitopes. A vaccine may comprise either MAP-LKQKSSNSRKKRSTS (SEQ ID NO:1), MAP-VKNKRTFLSPWISNI (SEQ ID NO:2), or some combination of the two MAPs.

Monoclonal antibodies (Mab) are monospecific antibodies. Monoclonal antibodies can be made by any method known in the art, for example, by fusing myeloma cells with spleen cells from a mouse that has been immunized with the desired antigen. Additionally, monoclonal antibodies can be humanized to remove possible reactions in humans. Alternatively, the monoclonal antibodies can be recombinant and can be made by any method known in the art. The monoclonal antibodies can then be purified by any method known in the art, for example, filtration, ion exchange chromatography, protein A/G affinity chromatography, or size exclusion chromatography.

The vaccine, pharmaceutical composition, method, and use of the present invention can be used for any animal, preferably mammals, such as mice or humans.

An adjuvant is a pharmacological or immunological agent that modifies the effect of other agents. In the case of the present invention, an adjuvant is an agent which makes the vaccine more effective by increasing the number of antibodies produced by the animal for the same number of peptide epitopes administered. Not all adjuvants can be used for vaccines. Only certain adjuvants are approved for use in mammals. Not all adjuvants approved for use in mammals are approved for use in humans.

The vaccine or pharmaceutical composition may be formulated by associating the peptide or monoclonal antibody with a pharmaceutically acceptable carrier. The pharmaceutically acceptable carrier must be compatible with the peptide or monoclonal antibody, and not deleterious to the animal. Examples of a pharmaceutically acceptable carrier include buffered saline. The vaccine or pharmaceutical composition may also be formulated in unit single or multiple unit dosage. The vaccine or pharmaceutical composition formulation may further comprise antibacterials such as amphotericin B, chlortetracycline, gentamicin, neomycin, polymyxin B, or streptomycin; thickening agents such as xanthan; stabilizers such as urea, sucrose, sorbitol, potassium glutamate, monosodium glutamate, lactose, histidine, glycine, gelatin, or ferric (III) nitrate; pH adjusters such as sodium hydroxide, sodium citrate, sodium borate, sodium bicarbonate, sodium acetate, potassium chloride, or phosphate buffers; surfactants such as sodium deoxycholate, polysorbate 80, polysorbate 20, polyoxyethylated octyl phenol, or polyocyethylene-9-10nonylphenol; antifoaming agents such as polydimethylsilozone; medium nutrients; preservative such as thimerosal, 2-phenoxyethanol, phenol, egg protein, or EDTA; or manufacturing residues.

The present invention can be used to both protect and treat an animal from anthrax toxin. An animal can be protected from anthrax toxin when one of the vaccines or pharmaceutical compositions of the present invention is administered prior to the animal's exposure to the anthrax bacterium or anthrax toxin. An animal can be treated for anthrax toxin when one of the vaccines or pharmaceutical compositions of the present invention is administered subsequent to the animal's exposure to the anthrax bacterium or anthrax toxin. Since the vaccines and pharmaceutical compositions of the present invention neutralize the anthrax toxin, if the animal is actively infected with the anthrax bacterium, antibiotics may be required in addition to the vaccine in order to kill or inhibit the growth of the anthrax bacterium.

EXPERIMENTAL DETAILS

I. Introduction

Protective antigen (PA), the binding subunit of anthrax toxin, is the major component in the current anthrax vaccine, but the fine antigenic structure of PA is not well-defined. To identify linear neutralizing epitopes of PA, 145 overlapping peptides covering the entire sequence of the protein were synthesized. Six monoclonal antibodies (mAbs) and antisera from mice specific for PA were tested for their reactivity to the peptides by enzyme-linked immunosorbent assays (ELISA). Three major linear immuno-dominant B-cell epitopes were mapped to residues L156 to S170, V196 to I210 and S312 to N326 of the PA protein. Two mAbs with toxin-neutralizing activity recognized two different epitopes in close proximity to the furin cleavage site in domain 1. The three dimensional complex structure of PA and its neutralizing mAbs 7.5G and 19D9 were modeled using molecular docking method providing models for the interacting epitope and paratope residues. For both mAbs, LeTx neutralization was associated with interference with furin cleavage, but they differed in effectiveness depending on whether they bound on the N- or C-terminal aspect of the cleaved products. The two peptides containing these epitopes that include amino acids L156-S170 and V196-I210 were immunogenic and elicited neutralizing antibody responses to PA.

Two monoclonal antibodies (mAbs) to PA have been reported previously, one known as 7.5G binds to domain 1 and can neutralize the cytotoxic activity of lethal toxin (LeTx) [13]. The other, mAb 10F4, binds to domain 4 and has weak neutralizing activity. In addition, four new anti-PA mAbs are described, of which only one neutralizes LeTx. The characterization of the B-cell epitopes in recognized by protective and non-protective mAbs is important to better understand the antigenic structure of this toxin and such information is useful for the design of vaccines and passive immune therapies against B. anthracis. Since has been identified as an effective subunit vaccine, identification of specific epitopes that provide the protection will allow their use as immunogens. Using mAbs and 145 overlapping peptides covering the entire sequence of PA the first linear neutralizing epitopes in domain 1 of PA was identified, and it was demonstrated that two peptides containing epitopes in domain I were capable of inducing strong LeTx-neutralizing antibody responses.

II. Methods and Materials

*B. anthracis*—*B. anthracis* Sterne strain 34F2 (pXO1+, pXO2−) was obtained from Dr. Alex Hoffmaster at the Center for Disease Control (Atlanta, Ga.). Bacterial cultures were grown in brain heart infusion (BHI) broth (Difco, Detroit, Mich.) at 37° C. for 18 h while shaking. Recombinant PA and LF were obtained from Wadsworth Laboratories, NYS Department of Health (Albany, N.Y.). Fragments of PA comprising one or more domains were expressed in *Escherichia coli* as previously described [13].

Mouse immunization with GALXM-PA conjugat—Female BALB/c (6-8 weeks old) were obtained from the National Cancer Institute (Bethesda, Md.). Two mice received an initial conjugate dose of 50 µl, while the third mouse was immunized with 100 µl of Galactoxylomannan-Protective Antigen (GalXM-PA) conjugate [14] in complete Freund's adjuvant (CFA). All mice were subsequently immunized with 50 µl of the conjugate in incomplete Freund's adjuvant (IFA) at day 14. Serum titers were analyzed to determine antigen response. Mice were boosted daily with 50 µl of the conjugate three days prior to fusion.

mAb production—Hybridomas making mAbs to PA were generated by standard techniques from splenocytes of GalXM-PA-immunized BALB/c mice [15]. The GalXM-PA conjugate had been synthesized to generate antibodies to GalXM for an independent study [14]. Additional PA-binding mAbs were made due to the availability of mice with high titers. Briefly, splenocytes from GalXM-PA-immunized mice were fused to NSO myeloma cells at a ratio of 4:1. NSO is the nonproducing mouse myeloma fusion partner. Two weeks later, hybridoma supernatants were screened by ELISA for Ab reactivity to PA. Hybridoma clones were then selected and stabilized by cloning twice in soft agar. The isotypes of the murine mAbs were established by ELISA using isotype-specific reagents (Southern Biotechnology, Birmingham, Ala.).

Determination of VH and VL sequences—Total RNA was isolated from hybridoma cell lines producing mAbs to EF using Trizol reagent (Gibco BRL, Gaithersburg, Md.) as per manufacturer's instructions. Briefly, 1 ml Trizol reagent was used per 106 log-phase hybridoma cells and 50 ng of RNA was used for cDNA synthesis with oligo (dT) primer and superscript II reverse transcriptase (Qiagen, Valencia, Calif.). Universal 5' (sense) variable region and specific 3' (antisense) constant region primers were used in a PCR reaction to generate cDNA encoding the variable domains of mAbs. The primers are as follows: 3'MsCγ: AGACCTATGGGGCTGT-TGTTTTGGC (SEQ ID NO:3); 3'MsCμ, GACATTTGG-GAAGGACTGACTCTC (SEQ ID NO:4); 3'MsCκ, TGGATACAGTTGGTGCAGCATCAGC (SEQ ID NO:5); 5'VHuni, TGAGGTGCAGCTGGAGGAGTC (SEQ ID NO:6); 5'Vκuni, GACATTCTGATGACCCAGTCT (SEQ ID NO:7). The PCR was performed using 1 ug of the cDNA template, with 2.5 mM each of deoxynucleoside triphosphate and 125 nM each primer under the following conditions with Taq polymerase (Roche, Mannheim, Germany): 94° C. for 1 min, 50° C. for 1 min, and 72° C. for 1.5 min for 40 cycles, followed by a final 10-min extension at 72° C. The amplified cDNAs were gel purified (Qiagen, Valencia, Calif.) and then sequenced at the Sequencing facility of the Cancer Center at the Albert Einstein College of Medicine.

LeTx neutralization assay—The LeTx neutralization assay used J774 macrophage-like cells treated with PA and LF, and mAb antitoxin activity was measured using the MTT [3,(4,5-dimethylthiazol-2-yl) 2,5-diphenyltetrazolium bromide] assay for cell viability. All incubations were done at 37° C. in a 5% CO2 atmosphere, 95% relative humidity. J774 cells were plated in 96-well flat bottom microtiter plates at a density of $3\times10^4$ cells/well in 200 µl DMEM supplemented with 10% fetal calf serum, 17 to 19 h prior to the assay. The following day, 100 µl of the cell supernatant was removed from wells containing J774 cells, and then incubated with 100 ng each of PA and LF and/or a range of dilutions of each antibody sample for 4 h. Cell viability was determined by the addition of 25 µl/well of a 5 mg/ml stock-solution of MTT, and the incubation continued for 2 h. The assay was terminated by addition of 100 µl/well of the extraction buffer (12% SDS, 45% DMF) and incubated overnight. The optical density values were measured at 570 nm (Labsystem Multiskan, Franklin, Mass.). All antibodies were tested at least three times, and the average was taken for wells receiving LeTx plus antibody or LeTx alone.

Proteolytic digestion of PA-PA was digested with furin (Sigma, St. Louis, Mo.) or trypsin (Promega, Madison, Wis.). For trypsin digestions, 10 µg of rPA in 150 mM NaCl2, 20 mM Tris, pH 8.2 was mixed with trypsin (1 µg/ml) for 30 min at RT in 20 µl volume. For furin digests, 10 µg of PA was incubated in 20 µl of 1 mM CaCl2, 1 mM β mercaptoenthanol, 0.5% TRITON X-100, 100 mM Hepes, pH 7.5 and mixed with 0.02 U-10 U of furin for 30 sec-15 min at 30° C. PA was cleaved by chymotrypsin (1:1; Sigma) for 30 min at 30° C. Digested products were separated on a 12% sodium dodecyl sulfate polyacrylamide gel electrophoresis (SDS-PAGE) [16]. The proteins were visualized by staining the gel with GelCode Blue Stain (Pierce, Rockford, Ill.).

SDS-PAGE and Western blot—To determine the domain location of the epitopes recognized by the various mAbs to PA, SDS-PAGE and Western blotting were employed. PA or its proteolytic digests were mixed with Laemmli sample buffer containing β-mercaptoethanol, boiled for 5 min, and then separated on SDS-PAGE gradient gel (10 to 20%). Proteins were then visualized by staining overnight with GelCode Blue Stain (Pierce, Rockford, Ill.). Proteins were transferred to nitrocellulose membrane (0.20 µm pore size) by electrophoretic transfer. The membranes were blocked with 5% dry milk in Tris-buffered saline/0.1% TWEEN 20 (TBST) and then incubated with mAbs 2.9H, 16A12, 19D9, or 20G7 overnight at 4° C. After washing with TBST, the membranes were incubated at room temperature (RT) for 1 h with horseradish peroxidase (HRP)-labeled goat isotype-specific antibody. The ECL chemiluminescence kit (Pierce, Rockford, Ill.) was used to reveal HRP activity according to the manufacturer's instructions.

Peptide Synthesis—To map the functional linear epitopes of PA, biotinylated soluble peptides representing the entire length of PA were synthesized as 15-mers, overlapping by 10 residues (total of 145 peptides) at the Proteomics Resource Center, Rockefeller University, New York, N.Y. All peptides were created using an Intavis MultiPep™ (Intavis, Koln, Germany) Wang resins (p-Alkoxy-benzyl alcohol) (Bachem, Torrance, Calif.) using F-moc (9-fluorenylmethyloxycarbonyl) nitrogen terminal-protected amino acids (Anaspec, San Jose, Calif.) [17]. Coupling reactions were conducted using HBTU (2-(1H-benzotriazole-1-yl)-1,1,3,3-tetramethyluronium hexafluorophosphate) and HOBT (1-hydroxybenzotriazole) in NMP (N-methylpyrrolidinone) as the primary solvent. All crude products were subsequently analyzed by reversed-phase HPLC (Waters Chromatography, Milford, Mass.) using an Acquity HPLC™ BEH130 C18 column. Individual peptide integrity was verified by electrospray ionization (ESI) mass spectrometry using a Thermo Scientific TSQ Vantage™ (Waltham, Mass.) LC/MS spectrometer system [18]. Peptides were supplied as a white powder soluble in water and stored at a concentration of 1 mg/ml.

ELISAs for PA and Peptides—Binding of antibody to PA was measured by ELISA. All incubations were done at 37° C. for 1 h. Briefly, a solution of rPA (1 µg/ml) in phosphate buffered saline (PBS) was used to coat polystyrene plates (Costar). The polystyrene plates were then blocked with 1% BSA/PBS and either immune sera or hybridoma supernatants were added. Primary antibody binding was detected using alkaline-phosphatase labeled goat anti-mouse antibody reagents. After addition of substrate, OD was read at 405 nm. Non-linear regression curve fit (one-site total binding) was used for calculation of dissociation constant values of mAbs 7.5G and 19D9 for PA samples. Plots, curve fits, and statistical analysis were performed using GraphPad Prism version 5.0a, GraphPad Software (San Diego Calif.).

For the peptide ELISAs, polystyrene plates were coated with 5 µg/ml streptavidin (100 µl/well) and kept overnight at 37° C. Then, the plates were blocked with 2% BSA in PBS (200 µl/well) for 1 h at 37° C. and then washed with 0.1% TWEEN 20 in PBS (PBST). Subsequently, biotinylated peptides (5 µg/ml) were added and incubated at RT for 1 h. After three washes with PBST, mAb or sera were added in dilution 1:100 or 1:500, respectively, in blocking buffer, and incubated for 2 h. The plates were again washed with PBST. Alkaline phosphatase-conjugated goat isotype-specific antibody was diluted 1:1,000 in blocking buffer, added to the plates and incubated for 1 h at 37° C. After another wash, alkaline phosphatase substrate was added to each well, allowed to develop for 20 min, and the absorbance at 405 nm was measured. These experiments were performed at least three times for each mAb. The background of each individual serum or mAb was determined in parallel, by using streptavidin-coated, peptide free wells. The cut-off value for real binding was defined as an absorbance value three times the average background value.

Isotype and IgG subclass analysis was performed as described above, and serial twofold dilutions of sera from immunized mice were added. Detection was performed with alkaline phosphatase-labeled goat anti-mouse IgG1, IgG2a, IgG2b and IgG3 at a 1:1000 dilution (Southern Biotechnology).

Competition ELISAs—mAb-mAb competition ELISAs were used to investigate the specificity of PA mAbs as described [19]. Briefly, a variable amount of one mAb was mixed with a constant amount of a second different isotype mAb and allowed to bind to PA immobilized in a polystyrene plate. Binding of the mAbs was detected by isotype specific alkaline-phosphatase conjugated goat anti-mouse reagent. However, in the case of the same isotypes, one mAb was chosen at random to be labeled with alkaline-phosphatase with a commercially available kit, following the manufacturer's instructions. In all instances, incubations were done at 37° C. for 1 h and absorbances were measured in a microtiter plate reader at 405 nm (Labsystems Multiskan).

Immunization—Six to eight week old female BALB/c mice (The Jackson Laboratory, Bar Harbor, Me.) were used for immunizations. The following peptides, LKQKSSN-SRKKRSTS (MAP-D5) (SEQ ID NO:1) and VKNKRTFL-SPWISNI (MAP-E1) (SEQ ID NO:2) were prepared on an eight-branched lysine backbone (peptide on MAP were from W.M. Keck Facility, Yale University, New Haven, Conn.). Mice were immunized subcutaneously with 100 µg of MAP-peptide in CFA on day 0, followed by subcutaneous booster injections of 100 µg of MAP-peptide in IFA on days 7 and 14. Control mice were immunized with the MAP core (Anaspec, San Jose, Calif.) in adjuvant and followed the same immunization schedule. Serum was obtained on days 0, 7, 14, 21, 35 and 49. All animal work was done in accordance with regulations of the Institute for Animal Studies at Albert Einstein College of Medicine.

Survival studies—Six to eight week old female A/JCr mice were injected intraperitoneally (i.p.) with 0.1 mg of mAb 19D9 2 h prior to intravenous (i.v.) infection with 104 bacterial cells of B. anthracis. Mice were monitored daily for mortality and morbidity and deaths recorded. All animal work was done in accordance with regulations of the Institute for Animal Studies at Albert Einstein College of Medicine.

Molecular modeling—Comparative protein structure models were generated for mAbs 7.5G and 19D9 based on the available similar structures of IgG2b and IgG1 molecules, respectively, (Protein Data Bank accession codes: 1 ibg and 3dvg) using Multiple Mapping Method [20] to generate a target-template sequence alignment and MODELLER [21] to generate the atomic models. mAbs 7.5G and 19D9 share 42% and 41% identical positions with 1 ibg and 3dvg template structures, respectively. Next, 10000 docking solutions were generated for each of the given antibodies with PA using the program FTDOCK [22]. The amino acid compositions of the putative epitopes of PA are known from the peptide library produced in this work, and these sequences can be found linearly displayed on PA. This information was used to screen and locate the most accurate complex structures. In some instances, some of the amino acids of a linear peptide segment are buried within PA structure, thus we developed a PERL program that searches the common surface between PA and the antibody for perfect matches with the amino acid composition of the reactive peptides (the PERL program uses VMD v1.862 for surface recognition). The resulting rigid body docked complexes were used as structural templates to build an optimized atomic structure with MODELLER [21].

Statistical analysis—All data were analyzed by the Student t test and survival analysis was done by log rank censoring long term survivors (Sigmastat, Chicago, Ill.).

III. Results

Generation and identification of PA-binding LeTx-neutralizing mAbs. Two hybridoma clones producing mAbs to PA (7.5G and 10F4) have been described previously [13] and these antibodies are further characterized in this study. All mice immunized with GalXM-PA conjugate in CFA responded to immunization with a serum antibody response to rPA (FIG. 1). The mouse with the highest Ab titer to PA was selected for spleen harvest and hybridoma generation, and the hybridoma supernatants were screened for reactivity toward PA. The endpoint ELISA titer with a minimal OD reading that was threefold higher than background was used as the criterion to select antibodies for the next stage of analysis. Four mAbs were recovered: three IgG1s (29H, 16A12 and 19D9) and one IgM (20G7).

Ig gene utilization. To determine the variable gene usage of the PA binding mAbs, the sequences of the heavy and light chain Ig mRNA of each mAb were determined. Total RNA from each hybridoma cell was isolated and reverse transcribed to generate cDNA. Then, the heavy and light chain cDNA were amplified by PCR using either VH or VK primers, respectively. Analysis of the sequences revealed that all mAbs are similar in molecular construction, using the same germline VH7183 and VKBD2 gene element (Table 1). For each mAb, the VH and VK domains were deposited in the GenBank database under the respective accession numbers listed.

not compete with any of the mAbs, implying that each recognized a different epitope on PA. From these experiments it can be seen that two mAb sets bind to the same epitopes.

Figure 3:
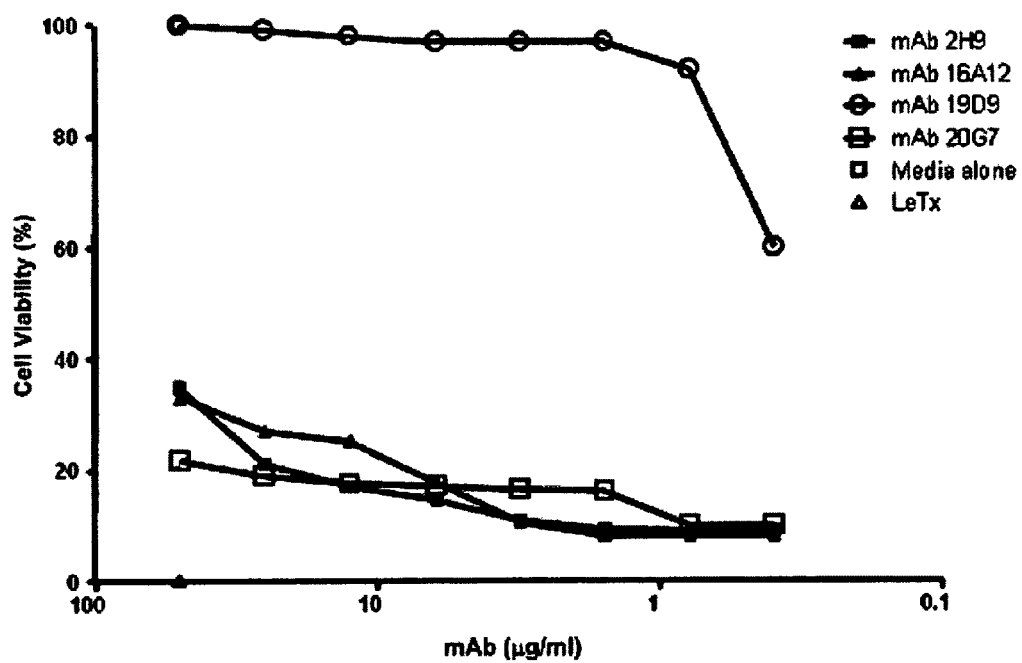
FIG. 3. Analysis of cellular toxicity in the presence of anti-PA mAbs by MTT assay. mAb 19D9 protects J774 macrophage monolayers against LeTx-mediated toxicity. mAbs 2H9, 16A12 and 20G7 had no inhibitory effect against LeTx-mediated toxicity. MTT assays were done three times with similar results.
Figures 4A, 4B, 4C:
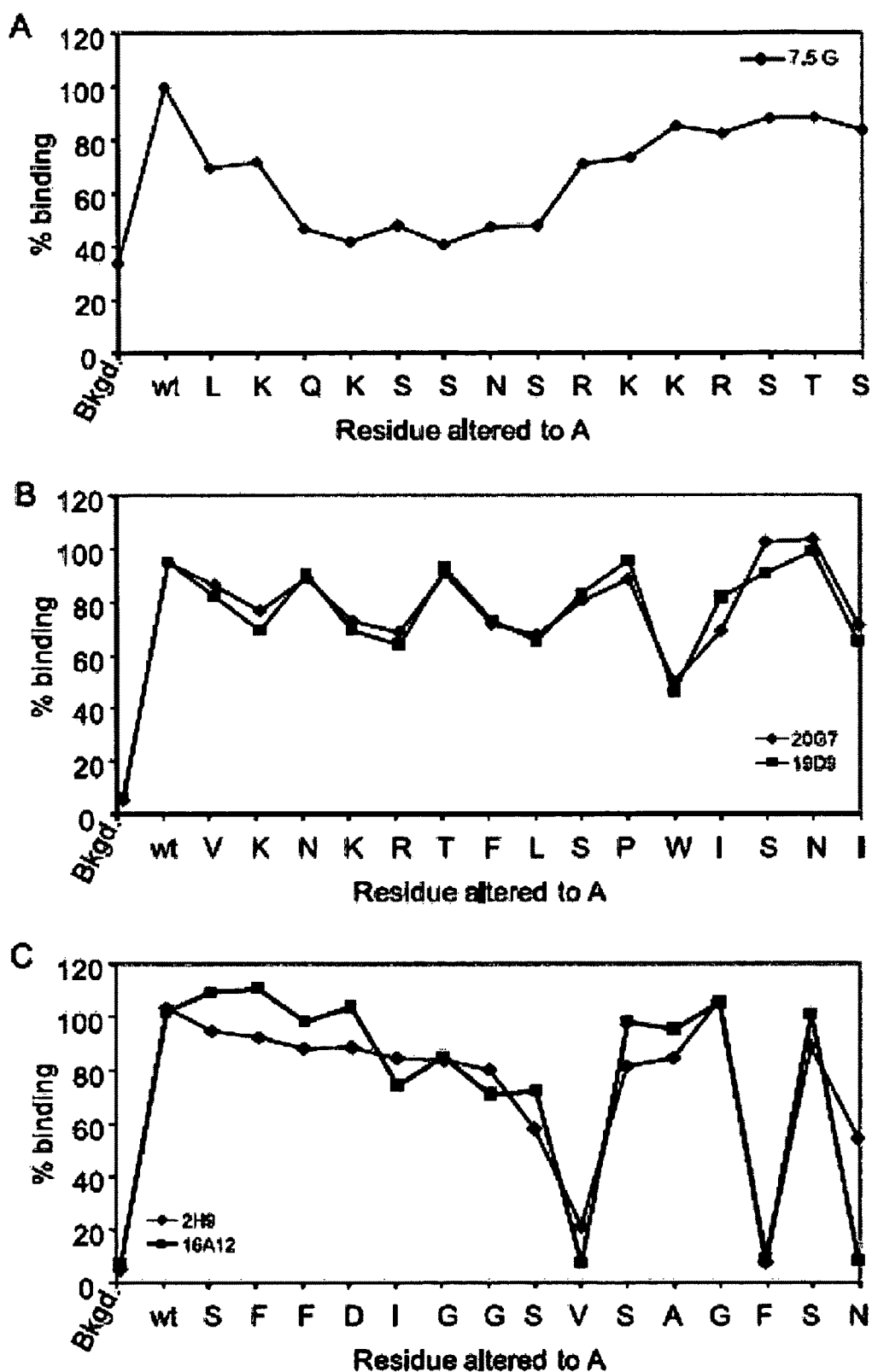
FIG. 4A-4C. An alanine walk to determine the critical residues in three identified epitopes. Each residue extending from L156-S170 (A), V196-I210 (B) or S312-N326 (C) was altered in turn to Ala or Gly (in the case if an Ala was present) and their reactivities with mAbs 7.5G, 29H, 19D9 and 20G7 were determined by ELISA. The OD readings of relative binding of mAbs to the alanine substituted peptides is expressed as % binding of each altered peptide with respect to wilt-type peptide, where the latter was considered the baseline maximum binding level. The background of each mAb was determined in parallel, by using streptavidin-coated, peptide free wells. The average value of three experiments is shown.
Figure 5:
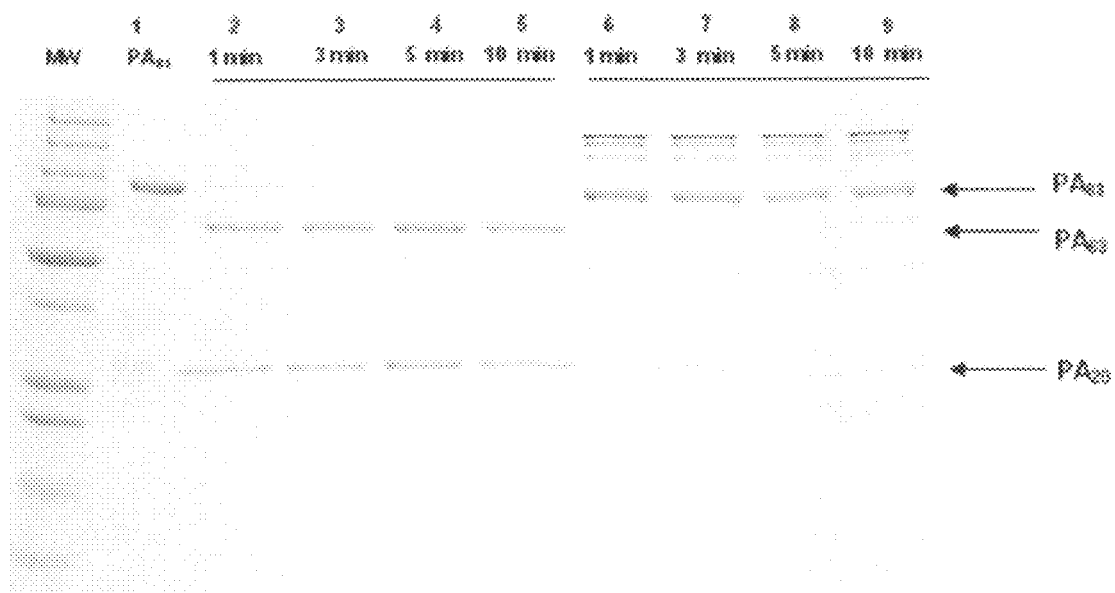
FIG. 5. Cleavage of PA83 with furin in the absence and presence of mAb 19D9. The mAb 19D9 was incubated with PA for 1 h at room temperature prior to the adding of protease. The samples were separated by reduced SDS-PAGE 10% gels and stained with COOMASSIE BLUE. MW: molecular weight marker; Lane 1: PA undigested; Lanes 2, 3, 4 and 5: PA+furin; Lanes 6, 7, 8 and 9: PA+furin+mAb.
Figure 6A:
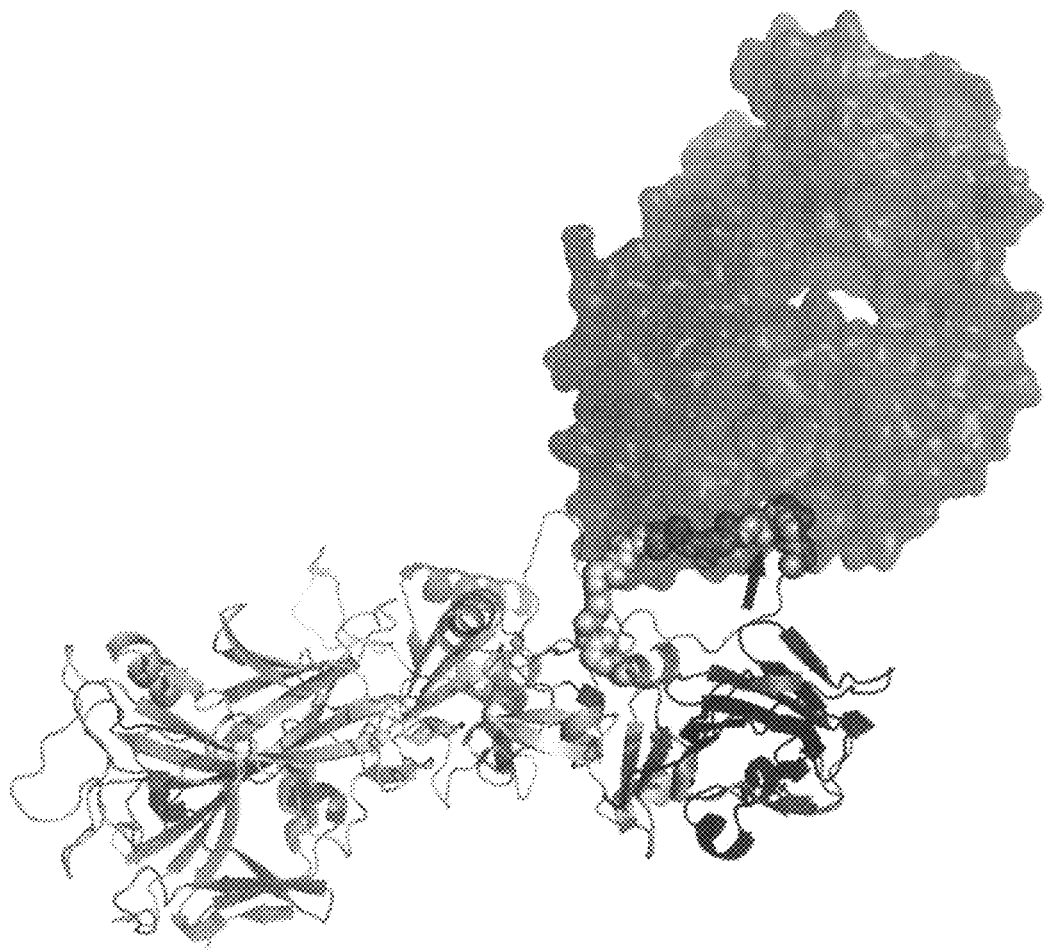
FIG. 6A-6B. Molecular modeling analysis of mAbs 7.5G and 19D9. (A) Docking of 7.5G mAb on PA protein. (B) Docking of 19D9 mAb on PA protein. PA protein is depicted as a ribbon representation, while the epitopes, which are found in domain 1, are shown as spheres. Arrows represent the furin site. mAbs are shown as space filling models.
Figure 6B:
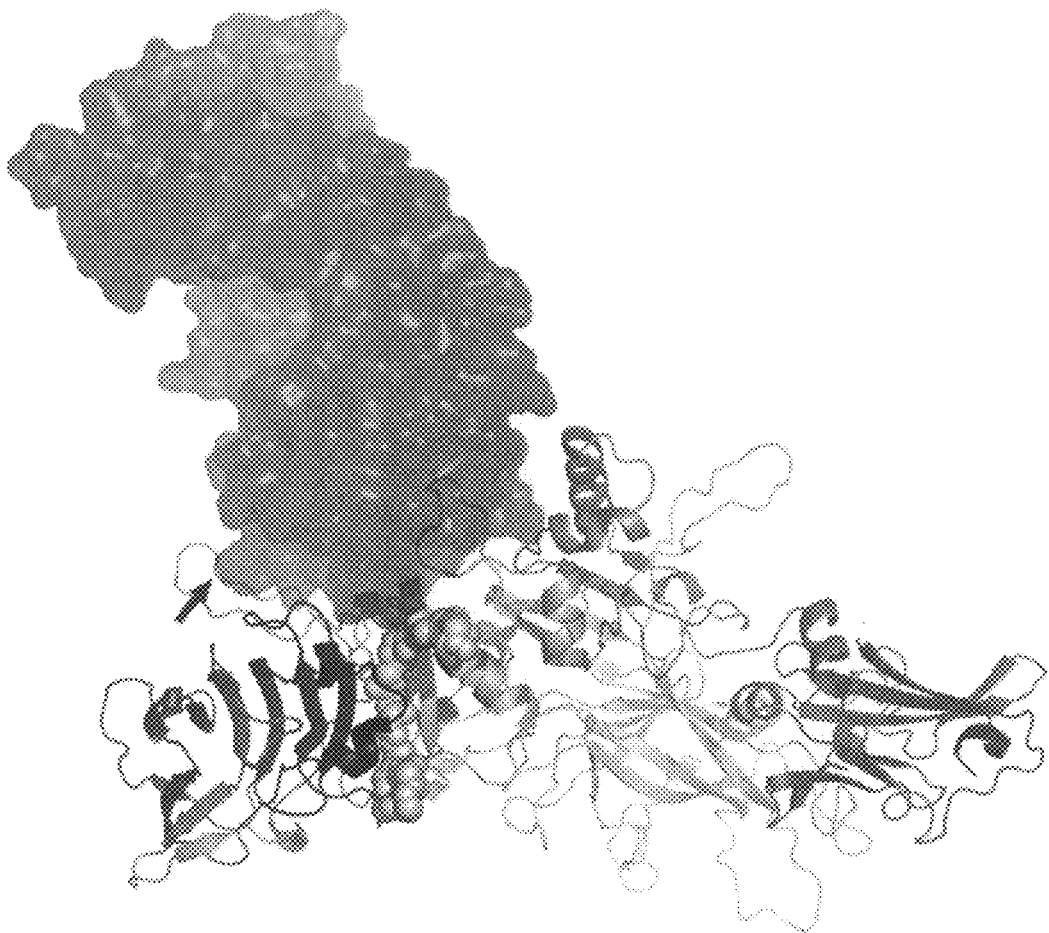
Figure 7:
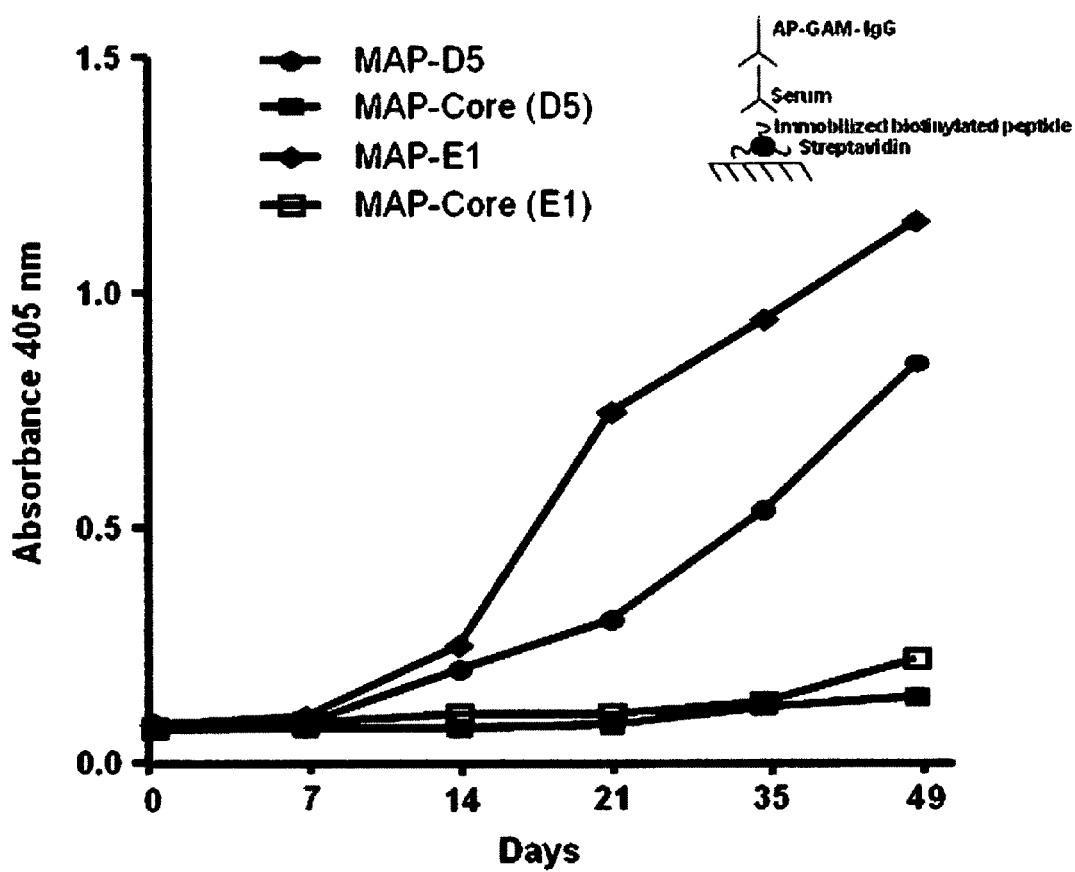
FIG. 7. Anti-peptide antibodies in MAP-D5- and MAP-E1-immunized mice. Female BALB/c mice (five animals per group) were immunized with 100 ug of MAP-D5 or MAP-E1 in CFA on day 0, and boosted with MAP-D5 or MAP-E1 in IFA on days 7 and 14, while control mice were immunized with MAP core in adjuvant. Sera from the different time points were diluted 1:500, and assayed for IgG anti-peptide antibodies by ELISA. Each point represents the average of five mice per treatment group. Insert, schematic of ELISA configuration used.
Figure 8:
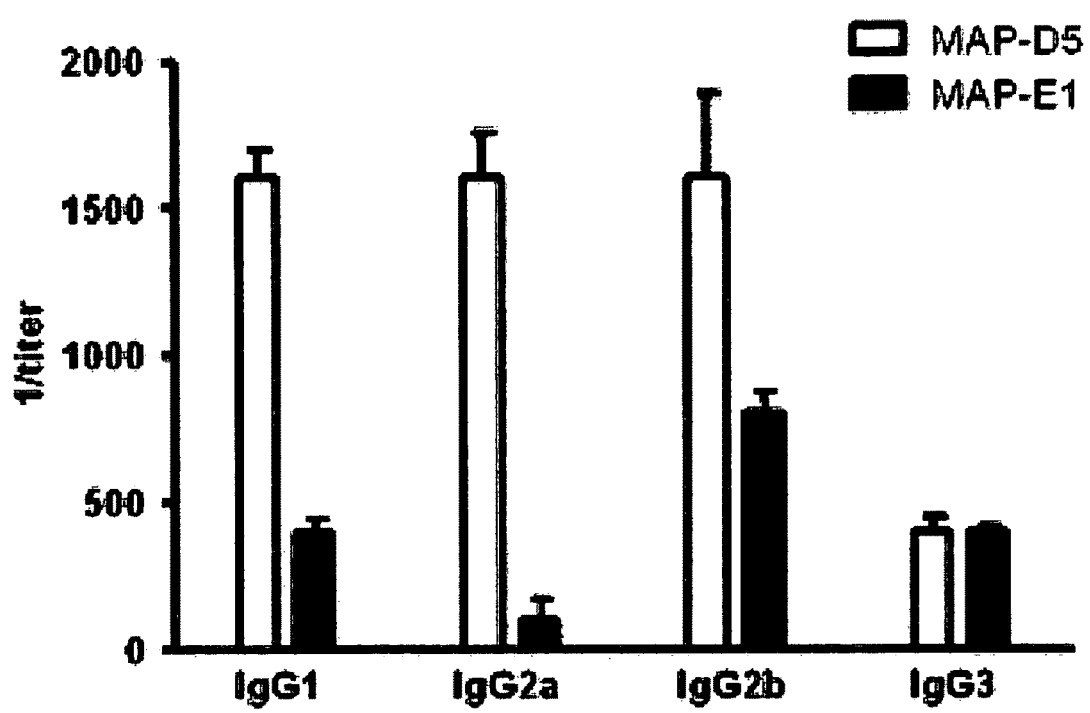
FIG. 8. IgG subclasses of anti-MAP-D5 and anti-MAP-E1 antibodies induced following immunization with MAP-D5 and MAP-E1. The subclasses of the IgG anti-peptide antibodies in day +49 sera from five MAP-D5-immunized mice and five MAP-E1-immunized mice were measured by ELISA.

Measurement of the affinity of the mAbs for PA was determined by ELISA. The Kd values of the identified antibodies were 5.877 nM for 7.5G and 0.2113 for 19D9.

mAbs effect on LeTx toxicity on macrophages. The ability of mAbs to protect macrophages against toxin-mediated cytotoxicity was studied. Each mAb was tested for LeTx neutralization with concentration adjustment (between 75 μg/ml to 0.5 μg/ml. Therefore, this screening method selected for mAbs that either protected at high levels of antibody or at lower antibody concentrations obtaining high neutralization activity. Only one mAb, 19D9, exhibited significant neutralization activity and this effect was dose dependent (FIG. 3).

mAbs effect on LeTx toxicity on mice. To examine further the ability of mAb 19D9 to neutralize LeTx, its protective efficacy was tested in vivo. The mAbs were administered to the mice (5 mice/group) by i.p., 2 h prior to i.v. infection with *B. anthracis* germinated cells. Control animals received PBS instead of antibody. Administration of mAb 19D9 prolonged survival of infected mice compared to control mice. In addi-

TABLE 1

Hybridoma families and mAb $V_H$ and $V_L$ usage

| Hybridoma | Neutralizing | Accession Number[1] | Variable Gene Elements[2] | | | |
|---|---|---|---|---|---|---|
| | | | $V_H$ | $J_H$ | $V_k$ | $J_K$ |
| 2H9 (IgG1) | No | FJ784743[a] FJ784747[b] | 7183 (5) (98.6%) | JH4 (1) (100%) | BD2 (7) (92.7%) | JK1 (93.8%) |
| 16A12 (IgG1) | No | FJ784744[a] FJ784748[b] | 7183 (97%) | JH4 (100%) | BD2 (84.7%) | JK1 (88.1%) |
| 19D9 (IgG1) | Yes | FJ784745[a] FJ784749[b] | 7183 (98%) | JH4 (100%) | BD2 (91.1%) | JK2/JK5 (2) (80%) |
| 20G7 (IgM) | No | FJ784746[a] FJ784750[b] | 7183 (100%) | JH4 (100%) | BD2 (84.0%) | JK1 (90.6%) |

Figure 2:
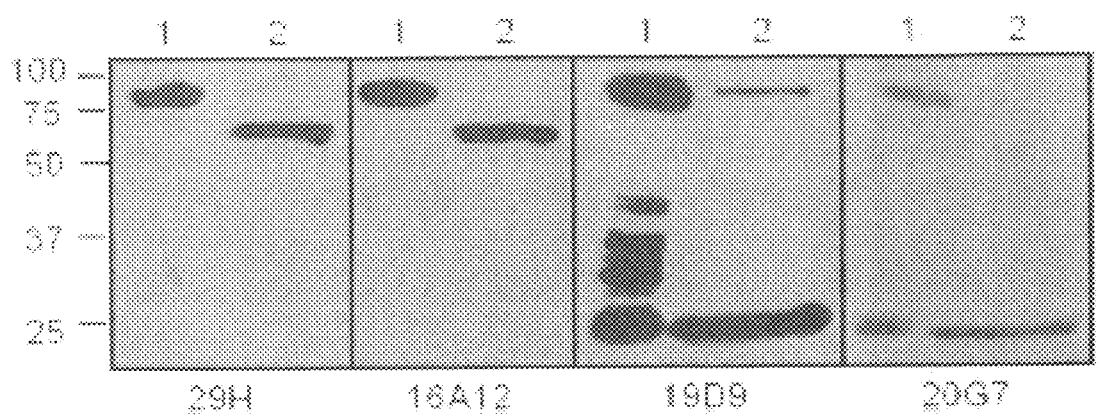
FIG. 2. Western immunoblot analysis of mAbs binding to PA. The samples were separated by reduced SDS-PAGE 10% gels and then transferred onto nitrocellulose membrane. The membranes were then incubated with mAbs 29H, 16A12, 19D9 or 20G7 as the primary antibody and a HRP-conjugated goat isotype-specific antibody as the secondary antibody. The bands were visualized by ECL chemiluminescence kit. Lane 1, rPA undigested; Lane 2, rPA+furin.

[1]Accession number for sequence in Genbank (Bethesda, MD).
[2]Variable gene usage assigned from homology searches. Number in parenthesis is percentage homology to the stated V region elements.
[a]Heavy chain
[b]Light chain mAb specificity for PA domains. To investigate the domains recognized by the various mAbs to PA, an ELISA detection assay was employed where the binding of the various antibodies to recombinant proteins expressing individual or combinations of different domains of PA as coated protein was studied. Two mAbs (19D9 and 20G7) were identified binding to domain 1 of PA, and two mAbs (29H and 16A12) were identified binding to expressed protein containing domains 2 to 4. These results were further confirmed by the binding of mAbs to enzyme digested PA by Western blot analysis. mAbs 29H and 16A12 bound to PA63 whereas mAbs 19D9 and 20G7 bound to PA20 (FIG. 2). Furthermore, the number of antigenic sites recognized by these antibodies were determined with competition ELISA. The mAb pairs of 19D9 and 20G7, and 29H and 16A12, competed with each other for binding to PA. In addition, mAbs 7.5G and 10F4 did tion, mAb 7.5G has also been shown to prolong the survival of BALB/c mice injected with toxin [13].

Mapping of the epitope recognized by mAbs. To identify the PA epitopes recognized by the mAbs, 15 mer peptides, overlapping by ten residues covering the entire sequence of PA, were used for epitope mapping. Three of the six antibodies recognized peptides spanning residues extending from L156-S170 and V196-I210 in domain 1 of PA (Table 2). These residues surround the furin cleavage site and hence provide insight on the mechanism to which 7.5G and 19D9 mAbs neutralize LeTx. Two other antibodies recognized the same peptide, extending from S312-N326. However, mAb 10F4 did not react with any peptide. This mAb seems to exhibit binding to a conformational epitope in domain 4 of PA.

TABLE 2

Peptide specificity of inAbs and mean of ELISA OD

Figures 9A, 9B:
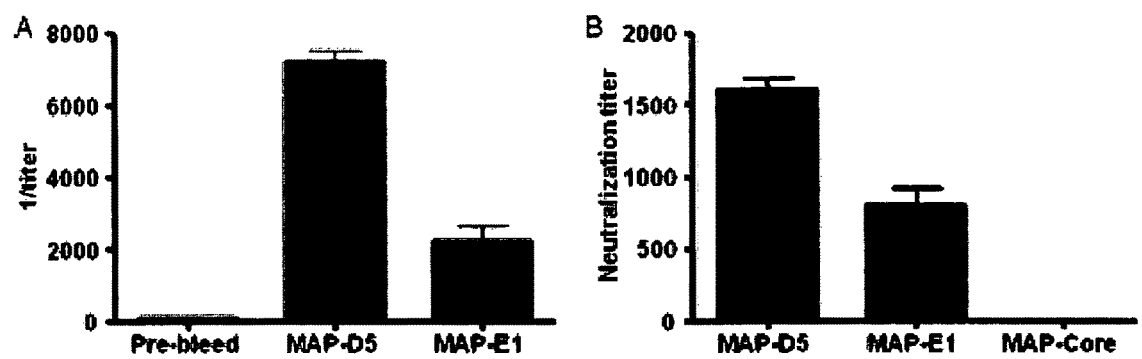
FIG. 9A-9B. Anti-PA antibodies in MAP-D5- and MAP-E1-immunized mice and LeTx-neutralizing activity on J774 macrophages. (A) Sera from day +49 were assayed for IgG anti-PA antibodies by ELISA. The values represent geometric means±standard deviation from five mice per treatment group. (B) Day +49 serum from mice immunized with MAP-D5 and MAP-E1 confer moderate protection to J774 macrophage monolayers against LeTx-mediated toxicity. Bars represent arithmetic mean of the highest neutralization titers from five mice per treatment group. MTT assays were done three times with similar results. Anti-MAP core sera conferred no protection.
| Monoclonal Antibody | Neutralizing | PA domain | Position | Sequence | Mean OD[1] | |
|---|---|---|---|---|---|---|
| | | Epitope Characterization | | | | |
| 7.5G | Yes | 1 | 156-170 | LKQKSSNSRKKRSTS | 0.908 | SEQ ID NO: 1 |
| 19D9 | Yes | 1 | 196-210 | VKNKRTFLSPWISNI | 0.569 | SEQ ID NO: 2 |
| 20G7 | No | 1 | 196-210 | VKNKRTFLSPWISNI | 0.322 | SEQ ID NO: 2 |
| 2H9 | No | 2 | 312-326 | SFFDIGGSVSAGFSN | 2.377 | SEQ ID NO: 8 |
| 16A12 | No | 2 | 312-326 | SFFDIGGSVSAGFSN | 2.259 | SEQ ID NO: 8 |
| 10F4 | Yes | 4 | NA | conformational epitope | NA | |

[1]Average of three replicates with a mAb dilution of 1:300 at which the antibody optical density (OD) reading was at least three times the average background value.

Next, a determination of whether there were any specific residues in the identified epitopes critical for the binding of each mAb was performed. Therefore, 15-mer peptides were synthesized such that every residue extending from L156-S170, V196-I210 or S312-N326 was changed to alanine with the exception of Ala322, which was changed to Gly. The reactivities with the mAbs, 7.5G, 19D9, 20G7, 16A12 or 29H, were assessed in the same manner described above. The alanine substitution of residues extending from Q158-S163 significantly reduced the binding of mAb 7.5G (FIG. 4A). Interestingly, alanine substitutions along the peptide sequence of V196-P205 had only a modest effect of binding mAbs19D9 and 20G7, whereas the presence of a bulky Trp residue underscores the importance of this residue in contacting both mAbs (FIG. 4B). In addition, alanine substitution of V320A, F324A and N326A in peptide S312-N326 abrogates the binding of mAbs 29H and 16A12 (FIG. 4C). The Val residue in the middle of the epitope and the Phe and Asn residues at the end of the epitope may create a particular structural conformation of the peptide allowing for mAb recognition. However, the G324A replacement did not alter the structural conformation of the peptide and therefore mAb binding paralleled the binding of wild-type peptide.

Cleavage of PA and dissociation of PA20. To examine whether mAb 19D9 binding affects dissociation of PA20 from PA63, PA was digested with 2 U of furin for 1, 3, 5, 7, 9, and 12 min intervals in the presence and absence of mAb. PA83 and its digested products were separated on a 12% sodium dodecyl sulfate polyacrylamide gel by electrophoresis (FIG. 5). The amounts of digested products, PA20 and PA63, increased in the absence of mAb 19D9 while the amount of undigested PA83 decreased over time. At all time intervals, there were less PA20 and PA63 and more PA83 when mAb 19D9 was present. Hence, mAb 19D9 significantly slows the proteolytic cleavage of PA83 to PA20 and PA63. mAb 7.5G has also been shown to slow furin proteolysis [13].

Molecular modeling. Three-dimensional molecular models were generated to study the complex formation between the two regions of PA that are specific to 7.5G and 19D9 neutralizing mAbs. The resulting docked complexes shown in FIG. 6A-B were derived from the crystal structure of PA and the modeled structure of mAbs 7.5G and 19D9. The docked complexes were filtered and refined using the sequence information provided from ELISA experimental results and the alanine scanning experiments of the epitopes.

In the case of mAb 7.5G, the reactive epitope, 158QKSSNS163 (SEQ ID NO:9) is represented by a long loop on the structure of PA, forming a linear epitope. For that of mAb 19D9, the epitope 206WISNI210 (SEQ ID NO:10) is also exposed, but on a smaller loop on the structure of domain 1. Inspection of the molecular surface of the binding sites indicated that the loops could provide an anchor point for binding the epitopes to both mAbs. The docked structures explain why there is no furin cleavage upon mAb binding as the bound complexes in both cases are protected from furin accession. In the case of 7.5G, the mAb directly binds to the loop that contains the furin cleavage site (FIG. 6A, arrow). For that of 19D9, the mAb binds to a different loop on PA, while able to sterically prohibit furin binding (FIG. 6B).

Reactivity of PA- and MAP-peptide-immunized mouse sera with peptides. Using the biotinylated peptides in ELISAs, the prevalence of antipeptide antibodies in sera of mice immunized with PA was explored. Peptides surrounding the furin cleavage site in domain 1 of PA were recognized by half of the mAbs, indicating that these epitopes are targets for a significant population of anti-PA antibodies. Antibodies to peptides spanning regions L156-S170 and V196-I210 were found in all sera with anti-PA reactivity. None of the control sera, negative for anti-PA antibodies, was found to be reactive with these peptides. Antibodies to the peptide spanning region S312-N326 in domain 2 of PA were not detected with any sera, thus indicating the rare presence of natural antibodies against this epitope.

Next, BALB/c mice were immunized with the octameric peptide MAP-LKQKSSNSRKKRSTS (MAP-D5) (SEQ ID NO:1) and MAP-VKNKRTFLSPWISNI (MAP-E1) (SEQ ID NO:2) in CFA, followed by two booster injections of MAP-D5 and MAP-E1 in IFA. This resulted in production of anti-peptide antibodies for both peptides tested. The IgG anti-peptide titer in MAP-D5 and MAP-E1-immunized mice rose by day 21 and continued to increase until day 49 when the mice were killed (FIG. 7). The IgG subclass distribution of anti-peptide antibodies is shown in FIG. 8. Mice immunized with MAP-D5 generated equal amounts of IgG1, IgG2a and IgG2b antibodies. Immunization with MAP-E1 resulted in the production of predominantly IgG2b anti-peptide antibodies. To further characterize the antigenic specificities present, ELISAs were performed to detect reactivity to PA. Anti-MAP-D5 IgG demonstrated significant titer (1/8,000) within 7 weeks (49 d postimmunization), while anti-MAP-E1 IgG reacted with PA at a titer of 1/2,000 (FIG. 9A). No IgG reactivity to PA was found in sera from mice immunized with the MAP core.

Anti-MAP-D5 and anti-MAP-E1 antibody effect on LeTx toxicity on macrophages. The protective efficacy of anti-peptide immune sera from all vaccinated groups against LeTx was evaluated with J774 cells. Cell viability was measured using the MTT method as described in Materials and Methods. The extent of cell death was expressed relative to a control containing LeTx or untreated cells. Day +49 immune sera from mice immunized with MAP-D5 and MAP-E1 conferred protection against the cytotoxic effects of LeTx with moderate protection up to 1/1,600 and 1/800 dilution, respectively (FIG. 9B). Sera from mice immunized with MAP core did not protect macrophages against LeTx cytotoxicity.

IV. Discussion

Six hybridoma clones expressing anti-PA mAbs that were generated by cell fusion techniques have been analyzed. Two PA neutralizing antibodies that efficiently protected animals from anthrax toxin challenge in vivo were identified. The two PA neutralizing antibodies most likely protect animals from anthrax toxin by preventing furin cleavage. The latter was based on epitope mapping studies, where the approach relied upon the use of overlapping synthetic peptides spanning the entire length of PA. The neutralization epitopes recognized by 7.5G and 19D9 mAbs were mapped to a region of PA comprising aa L156-S170 and aa V196-I210, respectively. In addition, the relevance of these linear epitopes has been confirmed by their reactivity to mouse immune sera with anti-PA antibodies, but not with control sera (pre-immune sera). To date, three neutralization epitopes in PA have been mapped to regions that contain the sites for cellular receptor binding, LF binding, and heptamer formation [24]. These two neutralization epitopes have been mapped to regions in PA that are in very close proximity to the furin cleavage site. The 3D complex structures of the mAbs and PA derived from molecular docking method illustrate a striking complementarity of fit between surfaces of mAb and surface exposed loops on domain 1 of PA. Peptide mutagenesis studies have highlighted these surface loops as the key regions for mAb interaction with PA, and defined critical binding residues on PA. In the docking models, 7.5G epitope is created by participation of surface loop residues Q158-S163, while for the 19D9 epitope is mapped to surface loop residues W206-I210.

mAbs 7.5G and 19D9 manifest differences in neutralizing activity despite closely related epitopes flanking the furin site. A recent report demonstrates that after mouse injection, PA83 is cleaved in vivo, that this cleavage is independent of cell surface binding and the proteolytic fragments, PA20 and PA63, circulate in the bloodstream [25]. In this regard, the finding that mAb 19D9 is more potent in its neutralizing capability than mAb 7.5G suggests that during intoxication free PA20 that is generated and left in the extracellular space may render mAb 7.5G less effective (epitope is located in PA20). In another scenario, binding of mAb 19D9 to the predicted surface-exposed epitope might create steric hindrance that would prevent efficient furin cleavage. Interestingly, the PA-binding affinities of mAbs 7.5G and 19D9 are different from each other, which may also correlate with their neutralization abilities. Peptide mutagenesis studies have delineated some details of mAb interaction with PA, and along with the docked models, have confirmed the probable mechanism of protection afforded by mAbs 7.5G and 19D9 against LeTx.

Furthermore, two non-neutralizing mAbs, 2H9 and 16A12, recognized a peptide the spans residues extending from S312-N326 in domain 2. According to the crystal structure of PA, this region encompasses part of the 2β2-2β3 loop and as stated above, undergoes structural rearrangements within the PA63 heptamer due to the acidified environment of the endosome, leading to the production of an extended β-barrel that inserts into the endosomal membrane [26-29]. In recent studies, the 2β2-2β3 loop was demonstrated to contain a dominant neutralizing epitope with the sequence S312-D315 [5, 8]. However, as discussed, the epitope recognized by mAbs 2H9 and 16A12 is mapped to 320VSAGFSN326, which is found to be a few amino acids after S312-D315. This illustrates that such a minor spacing can render an antibody with non-neutralizing capability. Interestingly, mAb 19D9 with strong toxin-neutralizing activity and mAb 20G7 with no neutralizing activity recognized the same epitope within domain 1. The key variation between these mAbs is their isotype; 19D9 is an IgG1, while 20G7 is an IgM. To be effective, antibodies must bind the target antigen and also invoke effector functions that will result in the removal of the antigen. The Fc region of the antibody is important in invoking this effector function. Since these two mAbs differ in there Fc region, a possible role could be due to their different interactions with their Fc receptors (FcRs), affording IgG1-FcR interaction more effective in removal of PA. This further reinforces the concept that antibodies to PA consist of heterogeneous groups.

The four mAbs use the same variable genes in VH and VL construction yet some differ in epitope specificity and protective efficacy. The finding that these mAbs each use the same gene elements in antibody construction implies that the response to PA is restricted in V region utilization. Given that this mAb set uses the same V regions, yet some differ in fine specificity, implies that the specificity differences arise from somatic mutations.

Three of 6 mAbs investigated were observed to bind at or near the furin site. This, combined with the finding that domain I can be highly immunogenic and elicit neutralizing antibodies [3] raises the possibility for a PA immunodominant antigen in the furin region cleavage area. The existence of strong B-cell epitopes near the furin cleavage site that can protect, presumably by interfering with proteolytic cleavage, raises the tantalizing possibility that recognizing epitopes in this area provided an advantage in mammalian evolution from the negative selection of B. anthracis infection. By selecting only those epitopes that confer protective immunity in designing a vaccine to direct the immune response to this region, exclusion of the epitopes responsible for deleterious immune responses can be manufactured. Immunization of BALB/c mice with MAP-D5 (peptide recognized by 7.5G) elicits anti-peptide antibodies. Immunization with peptide MAP-E1 specific for mAb 19D9 led to a peptide-specific response as well. An IgG response to MAP-D5 was identified with the highest anti-MAP-D5 titers to be a mixture of IgG1, IgG2a and IgG2b, while for anti-MAP-E1 titers the response to this peptide was predominately of IgG2b. This suggests a Th2-related response for induction of peptide antibodies. Sera from mice immunized with MAP-D5 and MAP-E1 also bound toxin and neutralized its biological activity. These epitopes thus proved useful to assess the epitope mapping potential of the peptide library and raised the importance of the fact that two selected peptides were indeed able to elicit neutralizing antibodies in the mouse. The ability of antibodies raised against a peptide to bind the cognate protein in its native state further supports the assignments of linear epitopes within PA.

Two independent amino acid sequences within domain 1 of PA that contain neutralizing linear epitopes have been identified. These epitopes lie in the N-terminal moiety of the protein, in region involved in furin cleavage. Identification of these immunodominant B-cell epitopes makes them attractive for epitope-based anthrax vaccines.

REFERENCES

1. Barth, H., et al., Binary bacterial toxins: biochemistry, biology, and applications of common *Clostridium* and *Bacillus* proteins. Microbiol. Mol Biol Rev, 2004. 68 (3): p. 373-402, table of contents.
2. Inglesby, T. V., et al., Anthrax as a biological weapon, 2002: updated recommendations for management. Jama, 2002. 287 (17): p. 2236-52.
3. Abboud, N. and A. Casadevall, Immunogenicity of *Bacillus anthracis* protective antigen domains and efficacy of elicited antibody responses depend on host genetic background. Clin Vaccine Immunol, 2008. 15 (7): p. 1115-23.
4. Flick-Smith, H. C., et al., A recombinant carboxy-terminal domain of the protective antigen of *Bacillus anthracis* protects mice against anthrax infection. Infect Immun, 2002. 70 (3): p. 1653-6.
5. Gubbins, M. J., et al., Production and characterization of neutralizing monoclonal antibodies that recognize an epitope in domain 2 of *Bacillus anthracis* protective antigen. FEMS Immunol Med Microbiol, 2006. 47 (3): p. 436-43.
6. Reed, D. S., et al., Mapping of antibody responses to the protective antigen of *Bacillus anthracis* by flow cytometric analysis. Cytometry, 2002. 49 (1): p. 1-7.
7. Rosovitz, M. J., et al., Alanine-scanning mutations in domain 4 of anthrax toxin protective antigen reveal residues important for binding to the cellular receptor and to a neutralizing monoclonal antibody. J Biol Chem, 2003. 278 (33): p. 30936-44.
8. Zhang, J., et al., The 2beta2-2beta3 loop of anthrax protective antigen contains a dominant neutralizing epitope. Biochem Biophys Res Commun, 2006. 341 (4): p. 1164-71.
9. Laffly, E., et al., Selection of a macaque Fab with framework regions like those in humans, high affinity, and ability to neutralize the protective antigen (PA) of *Bacillus anthracis* by binding to the segment of PA between residues 686 and 694. Antimicrob Agents Chemother, 2005. 49 (8): p. 3414-20.
10. Peterson, J. W., et al., Human monoclonal antibody AVP-21D9 to protective antigen reduces dissemination of the *Bacillus anthracis* Ames strain from the lungs in a rabbit model. Infect Immun, 2007. 75 (7): p. 3414-24.
11. Subramanian, G. M., et al., A phase 1 study of PAmAb, a fully human monoclonal antibody against *Bacillus anthracis* protective antigen, in healthy volunteers. Clin Infect Dis, 2005. 41 (1): p. 12-20.
12. Baillie, L., et al., Characterization of the human immune response to the UK anthrax vaccine. FEMS Immunol Med Microbiol, 2004. 42 (2): p. 267-70.
13. Rivera, J., et al., A monoclonal antibody to *Bacillus anthracis* protective antigen defines a neutralizing epitope in domain 1. Infect Immun, 2006. 74 (7): p. 4149-56.
14. De Jesus, M., et al., Capsular localization of the *Cryptococcus neoformans* polysaccharide component galactoxylomannan. Eukaryot Cell, 2009. 8 (1): p. 96-103.
15. de StGroth, S. F. and D. Scheidegger, Production of monoclonal antibodies: strategy and tactics. J Immunol Methods, 1980. 35 (1-2): p. 1-21.
16. Laemmli, U. K., Cleavage of structural proteins during the assembly of the head of bacteriophage T4. Nature, 1970. 227 (5259): p. 680-5.
17. Wellings, D. A. and E. Atherton, Standard Fmoc protocols. Methods Enzymol, 1997. 289: p. 44-67.
18. Beavis, R. C. and B. T. Chait, Matrix-assisted laser desorption ionization mass-spectrometry of proteins. Methods Enzymol, 1996. 270: p. 519-51.
19. Casadevall, A., J. Mukherjee, and M. D. Scharff, Monoclonal antibody based ELISAs for cryptococcal polysaccharide. J Immunol Methods, 1992. 154 (1): p. 27-35.
20. Rai, B. K. and A. Fiser, Multiple mapping method: a novel approach to the sequence-to-structure alignment problem in comparative protein structure modeling. Proteins, 2006. 63 (3): p. 644-61.
21. Sali, A. and T. L. Blundell, Comparative protein modelling by satisfaction of spatial restraints. J Mol Biol, 1993. 234 (3): p. 779-815.
22. Gabb, H. A., R. M. Jackson, and M. J. Sternberg, Modelling protein docking using shape complementarity, electrostatics and biochemical information. J Mol Biol, 1997. 272 (1): p. 106-20.
23. Baldari, C. T., et al., Anthrax toxins: A paradigm of bacterial immune suppression. Trends Immunol, 2006. 27 (9): p. 434-40.
24. Brossier, F., et al., Functional analysis of *Bacillus anthracis* protective antigen by using neutralizing monoclonal antibodies. Infect Immun, 2004. 72 (11): p. 6313-7.
25. Moayeri, M., J. F. Wiggins, and S. H. Leppla, Anthrax protective antigen cleavage and clearance from the blood of mice and rats. Infect Immun, 2007. 75 (11): p. 5175-84.
26. Petosa, C., et al., Crystal structure of the anthrax toxin protective antigen. Nature, 1997. 385 (6619): p. 833-8.
27. Benson, E. L., et al., Identification of residues lining the anthrax protective antigen channel. Biochemistry, 1998. 37 (11): p. 3941-8.
28. Nassi, S., R. J. Collier, and A. Finkelstein, PA63 channel of anthrax toxin: an extended beta-barrel. Biochemistry, 2002. 41 (5): p. 1445-50.
29. Santelli, E., et al., Crystal structure of a complex between anthrax toxin and its host cell receptor. Nature, 2004. 430 (7002): p. 905-8.

What is claimed is:

1. A purified peptide consisting of the amino acid sequence LKQKSSNSRKKRSTS (SEQ ID NO:1) or the amino acid sequence VKNKRTFLSPWISNI (SEQ ID NO:2).

2. The purified peptide of claim 1 consisting of the sequence LKQKSSNSRKKRSTS (SEQ ID NO:1).

3. The purified peptide of claim 1 consisting of the sequence VKNKRTFLSPWISNI (SEQ ID NO:2).

4. An anthrax vaccine comprising a multiple antigenic peptide comprising a lysine backbone and multiple peptide epitopes attached to the backbone, wherein the multiple peptide epitopes comprise multiple copies of one or both of the amino acid sequences of the peptide of claim 1.

5. The vaccine of claim 4 wherein the multiple antigenic peptide comprises the sequence LKQKSSNSRKKRSTS (SEQ ID NO:1).

6. The vaccine of claim 4 wherein the multiple antigenic peptide comprises the sequence VKNKRTFLSPWISNI (SEQ ID NO:2).

7. The vaccine of claim 4, wherein the multiple antigenic peptide is octameric.

8. The vaccine of claim 4, wherein the vaccine comprises an adjuvant.

9. A method to treat or immunize an animal against the cytotoxic effects of anthrax toxin, the method comprising administering to the animal the vaccine of claim 4.

10. The method of claim 9, wherein the multiple antigenic peptide in the vaccine comprises the sequence LKQKSSNSRKKRSTS (SEQ ID NO:1).

11. The method of claim 9, wherein the multiple antigenic peptide in the vaccine comprises the sequence VKNKRTFLSPWISNI (SEQ ID NO:2).

12. A method of making a vaccine comprising formulating a multiple antigenic peptide of claim 1 in a dosage form for treating or immunizing an animal against the cytotoxic effects of anthrax toxin.

13. The method of claim 9, wherein the animal is human.

14. The vaccine of claim 4 wherein the multiple antigenic peptide comprises between two and fourteen multiple peptide epitopes attached to the backbone.

15. The vaccine of claim 4 wherein the multiple antigenic peptide comprises between four and ten multiple peptide epitopes attached to the backbone.

* * * * *

SEQUENCE LISTING

<160> NUMBER OF SEQ ID NOS: 10

<210> SEQ ID NO 1
<211> LENGTH: 15
<212> TYPE: PRT
<213> ORGANISM: bacillus anthracis

<400> SEQUENCE: 1

-continued

Leu Lys Gln Lys Ser Ser Asn Ser Arg Lys Lys Arg Ser Thr Ser
1               5                   10                  15

<210> SEQ ID NO 2
<211> LENGTH: 15
<212> TYPE: PRT
<213> ORGANISM: Bacillus anthracis

<400> SEQUENCE: 2

Val Lys Asn Lys Arg Thr Phe Leu Ser Pro Trp Ile Ser Asn Ile
1               5                   10                  15

<210> SEQ ID NO 3
<211> LENGTH: 25
<212> TYPE: DNA
<213> ORGANISM: artificial
<220> FEATURE:
<223> OTHER INFORMATION: primer for 3'MsCgamma

<400> SEQUENCE: 3
agacctatgg ggctgttgtt ttggc                                    25

<210> SEQ ID NO 4
<211> LENGTH: 24
<212> TYPE: DNA
<213> ORGANISM: artificial
<220> FEATURE:
<223> OTHER INFORMATION: primer for 3'MsCmu

<400> SEQUENCE: 4
gacatttggg aaggactgac tctc                                     24

<210> SEQ ID NO 5
<211> LENGTH: 25
<212> TYPE: DNA
<213> ORGANISM: artificial
<220> FEATURE:
<223> OTHER INFORMATION: primer for 3'MsCkappa

<400> SEQUENCE: 5
tggatacagt tggtgcagca tcagc                                    25

<210> SEQ ID NO 6
<211> LENGTH: 21
<212> TYPE: DNA
<213> ORGANISM: artificial
<220> FEATURE:
<223> OTHER INFORMATION: primer for 5'VHuni

<400> SEQUENCE: 6
tgaggtgcag ctggaggagt c                                        21

<210> SEQ ID NO 7
<211> LENGTH: 21
<212> TYPE: DNA
<213> ORGANISM: artificial
<220> FEATURE:
<223> OTHER INFORMATION: primer for 5'Vkappauni

<400> SEQUENCE: 7
gacattctga tgacccagtc t                                        21

<210> SEQ ID NO 8
<211> LENGTH: 15
<212> TYPE: PRT
<213> ORGANISM: bacillus anthracis -continued

```
<400> SEQUENCE: 8

Ser Phe Phe Asp Ile Gly Gly Ser Val Ser Ala Gly Phe Ser Asn
1               5                   10                  15

<210> SEQ ID NO 9
<211> LENGTH: 6
<212> TYPE: PRT
<213> ORGANISM: bacillus anthracis

<400> SEQUENCE: 9

Gln Lys Ser Ser Asn Ser
1               5

<210> SEQ ID NO 10
<211> LENGTH: 5
<212> TYPE: PRT
<213> ORGANISM: bacillus anthracis

<400> SEQUENCE: 10

Trp Ile Ser Asn Ile
1               5
```